United States Patent [19]

Paradis et al.

[11] Patent Number: 5,190,067
[45] Date of Patent: Mar. 2, 1993

[54] DIRECTIONAL FLOW CONTROL

[75] Inventors: Joseph R. Paradis, 17 Hickory Forest Dr., Hilton Head Island, S.C. 29926; Peter N. Kotsifas, Fiskdale, Mass.

[73] Assignee: Nypro, Inc., Clinton, Mass. ; by Peter N. Kotsifas

[21] Appl. No.: 804,811

[22] Filed: Dec. 9, 1991

Related U.S. Application Data

[63] Continuation-in-part of Ser. No. 530,097, May 29, 1990, Pat. No. 5,070,905.

[51] Int. Cl.$^5$ .............................................. F16K 15/14
[52] U.S. Cl. ................................... 137/1; 137/512.3; 137/606; 251/149.1; 251/149.5; 604/83
[58] Field of Search ................ 137/854, 1, 512, 512.3, 137/606; 251/149.1, 149.4, 149.5, 149.7; 604/82, 83, 86

[56] References Cited

U.S. PATENT DOCUMENTS

| 4,000,740 | 1/1977 | Mittleman | 604/86 |
| 4,405,316 | 9/1983 | Mittleman | 604/86 |
| 4,610,276 | 9/1986 | Paradis | 604/86 X |
| 4,683,916 | 8/1987 | Raines | 251/149.1 X |
| 4,874,369 | 10/1989 | Kulle | 604/86 |
| 5,070,905 | 12/1991 | Paradis | 604/86 X |

*Primary Examiner*—Robert G. Nilson
*Attorney, Agent, or Firm*—George E. Kersey

[57] ABSTRACT

A flow control device in which flow channels converge in a housing containing an injection site and a pre-biased flow control diaphragm. The injection site may include a diaphragm. The diaphragm can be acted upon by an internal actuator or plunger that extends into one of the flow channels where the plunger can be engaged by an external member such as a Luer fitting. The actuator or plunger may be of rigid or flexible construction is at the entry position of an intermediate channel and extends to an output channel of the injection site.

19 Claims, 8 Drawing Sheets

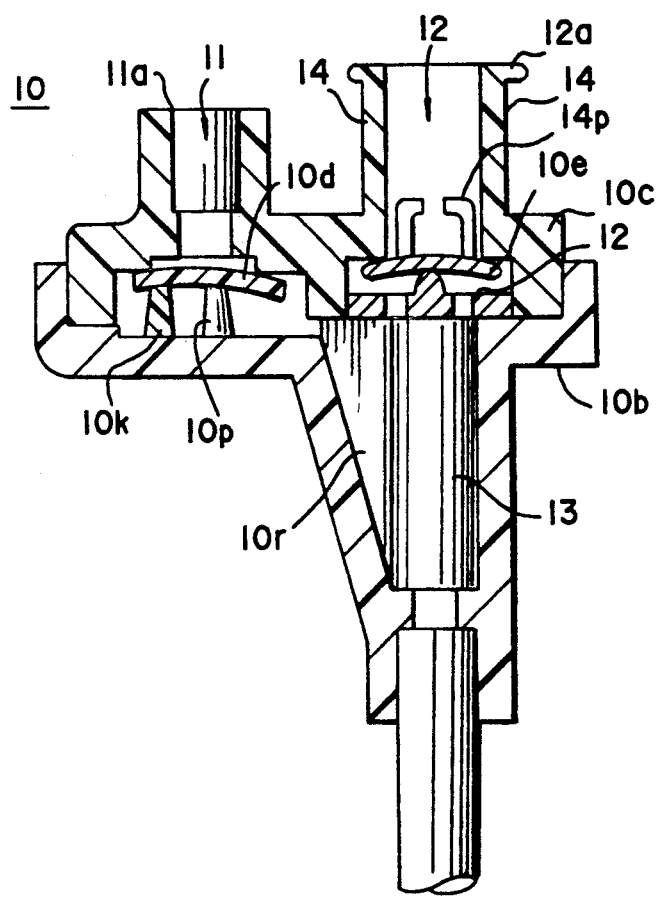
FIG.IA

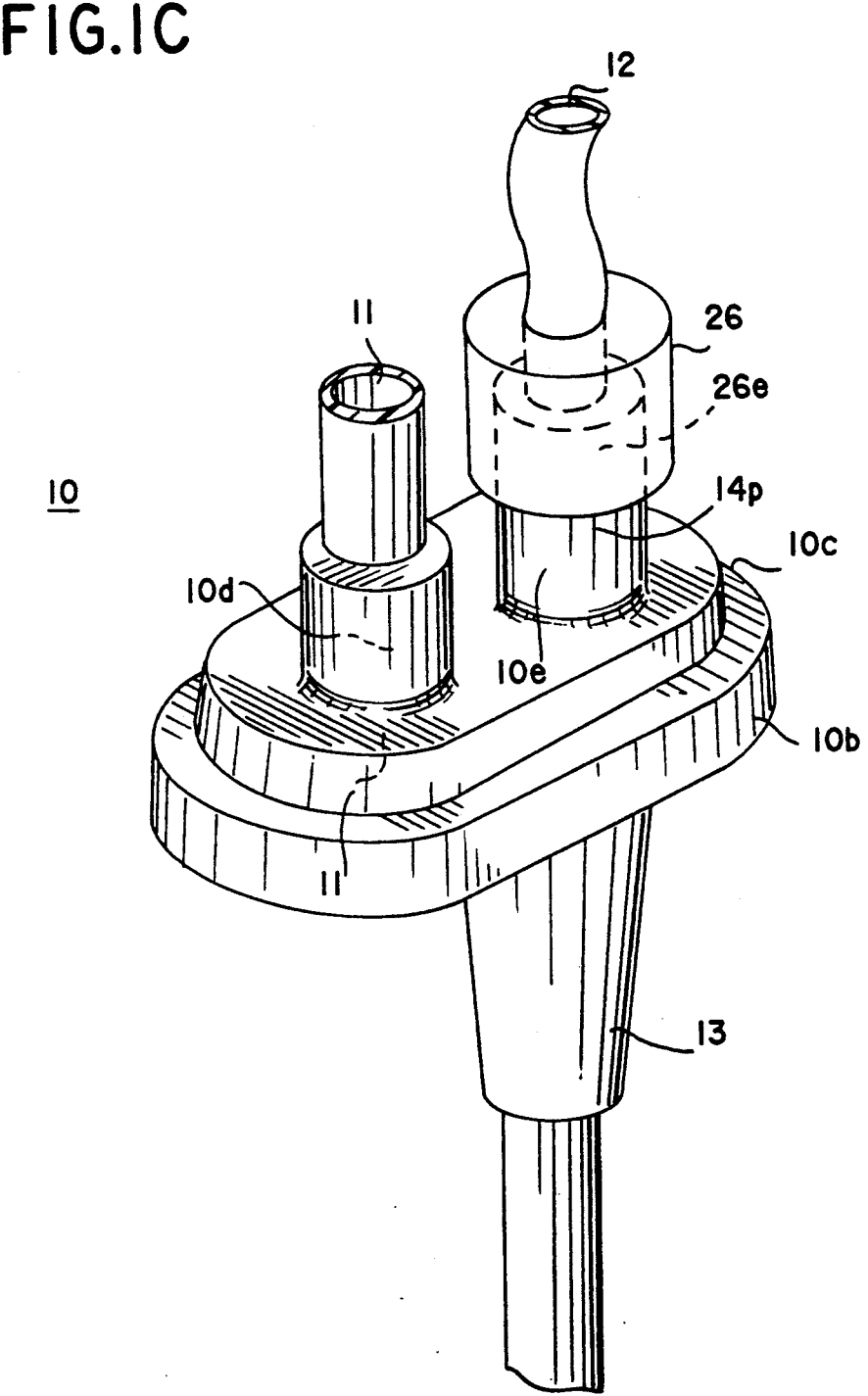
FIG.IC

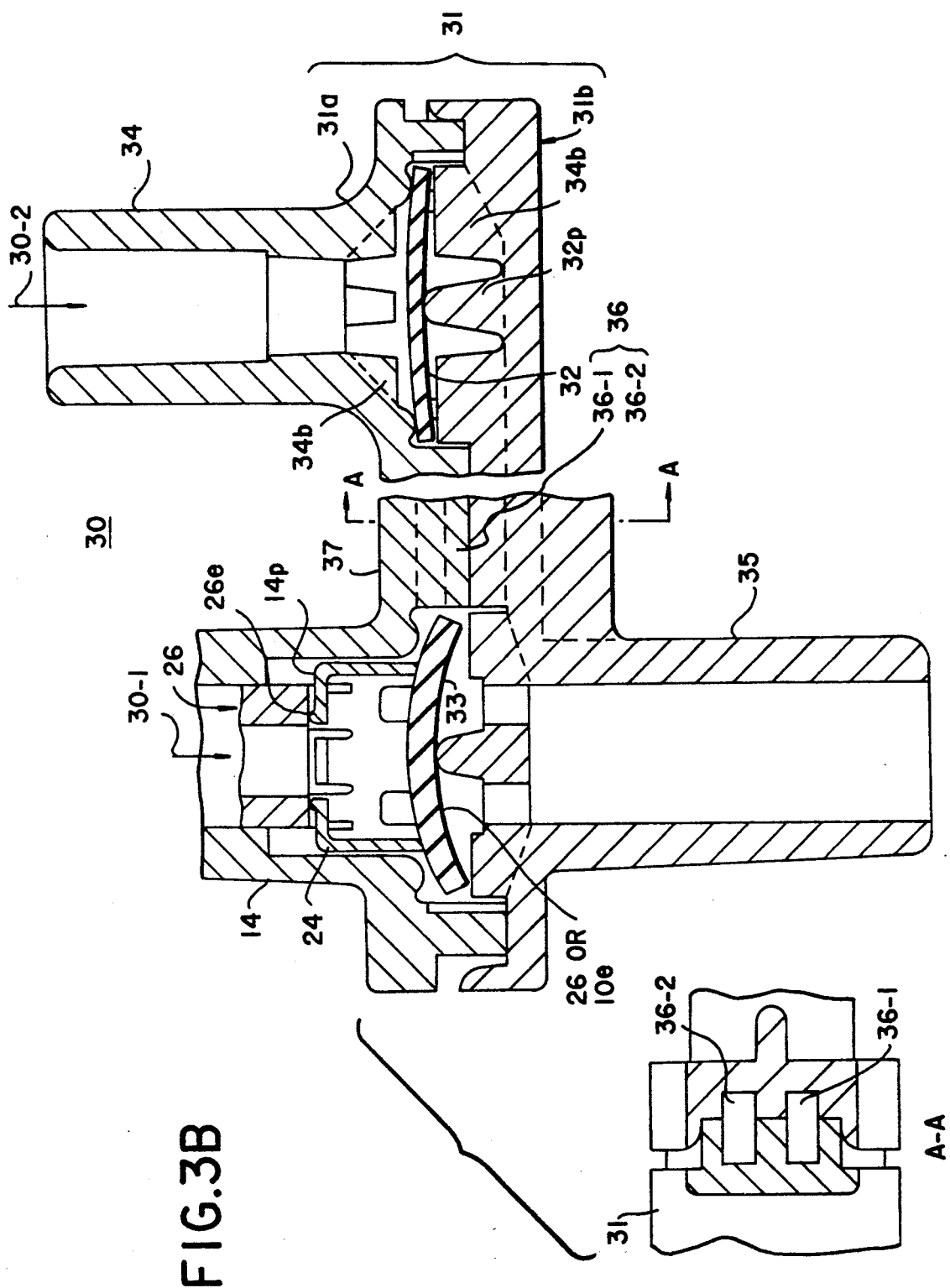

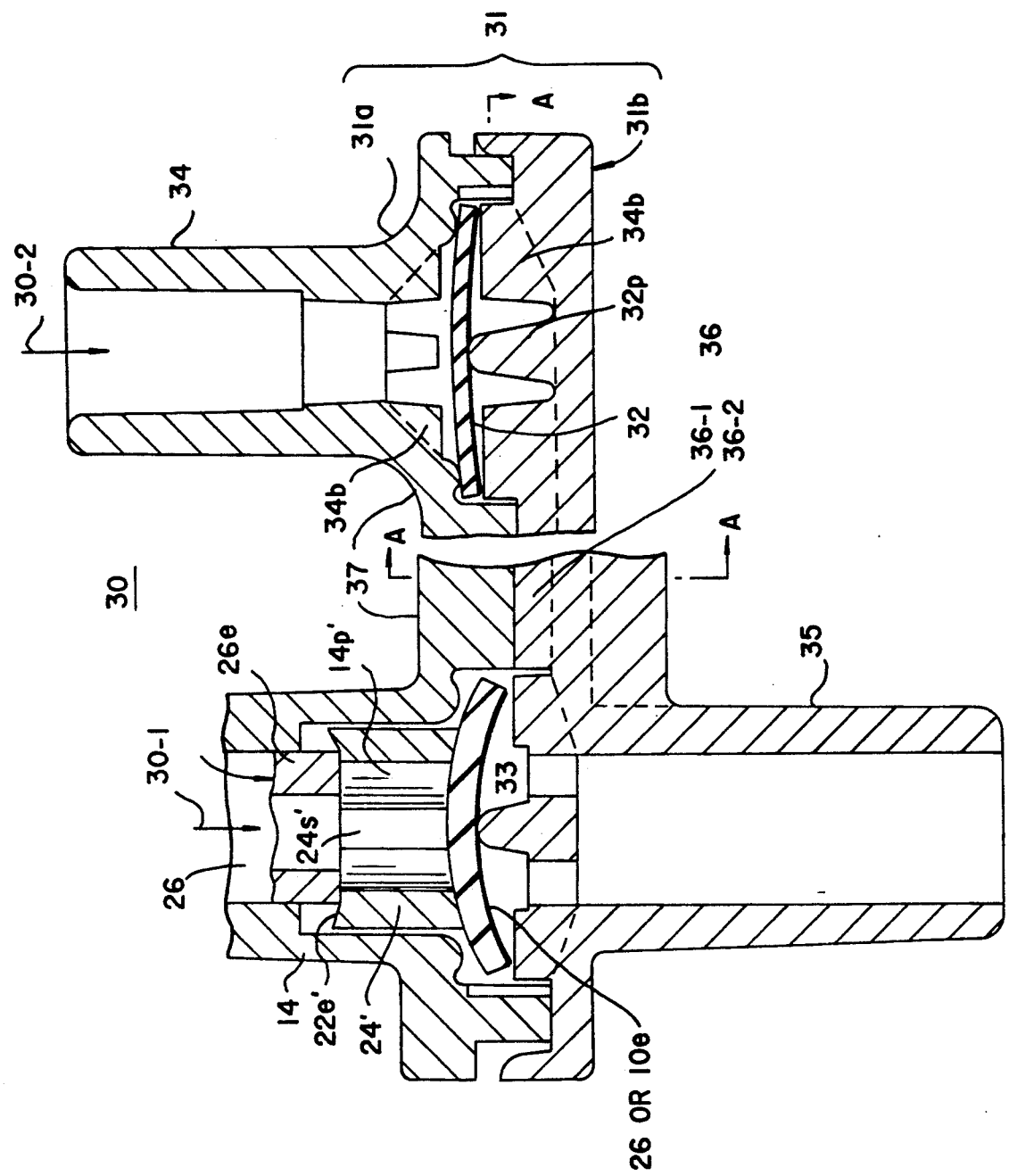

DIRECTIONAL FLOW CONTROL

BACKGROUND OF THE INVENTION

This is a continuation-in-part of Ser. No. 07/530,097 filed May, 29, 1990, U.S. Pat. No. 5,070,905. This invention relates to flow control and more particularly, to the directional control of fluid flow and injected fluids.

It often is desirable to control the flow of fluid such as liquids and gases. A common device for that purpose is known as a "check" valve, or a "Y" fitting. The check valve functions by the deflection of an elastomeric element towards and away from a valve seat. The deflection is towards the valve seat in order to prevent flow, and away from the seat to permit flow. In a "Y" there can be a check valve and an injection site.

In some cases the control of fluid flow is with respect to a multiplicity of channels that have varying degrees of convergence with one another. A typical multichannel arrangement makes use of connectors which permit the intercoupling of flow channels as desired. For example, when two channels are to be joined selectively to permit a common output from a single channel, the connector can take the form of a fitting that resembles a "Y".

The inclusion of control valves in the various lines leading to a coupler can pose a number of complications. The inclusion of separate control elements can cause difficulties in assuring proper sealing. A common point of leakage in a line often occurs where the line has been severed in order to receive a control element. In addition, the inclusion of separate control elements in various lines leading to a coupler does not always provide the most efficient control over fluid flow.

One solution for overcoming difficulties associated with prior art valves that control flow on multiple channels is set forth in U.S. Pat. No. 4,610,276 ("'276") which issued Sep. 9, 1986. This patent discloses a directional flow control valve with a main channel for the through-flow of fluid and a branch channel connected to the main channel at an intermediate position. This permits the convergence of flow through the main channel with flow through the branch channel. At the convergence of the two channels, there is a diaphragm for controlling the flow between the two channels. The diaphragm is clamped and bowed under pressure into the inlet of the branch channel. The application of pressure to the diaphragm assures the sealing of the branch channel against flow diverted from the main channel.

There also is a common housing in the '276 patent for the main flow channel and the branch flow channel. The diaphragm is bowed into the branch channel by a set of prongs with tips that extend as projections from a shelf that is common to the branch and main channels. The bowing of the diaphragm is asymmetric, and greater pressure is applied away from the region of outflow from the branch channel.

While the diaphragm of the '276 patent operates properly in most cases, there is the possibility that the diaphragm will fail to seat properly.

Another valve arrangement for dealing with main and branch channels is disclosed in U.S. Pat. No. 4,874,369 which issued Oct. 17, 1989. This arrangement employs an injection site in conjunction with a valve, illustratively of the duck-bill type, in a configuration that is complex, costly and difficult to manufacture. In addition, duck-bill valves of the type contemplated by the '369 patent have proved to be unreliable in practice, with such difficulties as failure to seal properly.

Other arrangements which relate to the control of fluid flow are disclosed in Osborne U.S. Pat. No. 2,270,468; Goott et al U.S. Pat. No. 3,370,305; Craft U.S. Pat. No. 3,457,933; Rosenberg 3,572,375, 3,650,093 and 3,710,942; Bobo U.S. Pat. No. 3,886,937; Melnick U.S. Pat. No. 3,891,000; Mittleman U.S. Pat. No. 4,000,740 and 4,405,316; Stevens 4,000,739; Zedes et al U.S. Pat. No. 4,005,710; Mittleman et al 4,048,996 and 4,133,441; Rushkie et al U.S. Pat. No. 4,222,407; Sheehan et al 4,294,249; Spademan 4,338,934; Paradis 4,415,003; Spector et al 4,424,833; Edwards et al 4,566,493; Goodell 4,596,265; Suzuki et al 4,610,674 and Holtermann et al 4,958,661; EPO No. 0109903; France No. 2004771 and UK No. 2033230. None of these arrangements provide enhanced flow control where there is diversion of fluid flow from one direction to another.

In addition, all of the foregoing valves require the presence of fluid pressure in order to operate the diaphragm, either by exerting pressure to open the diaphragm or by using reverse pressure to close the diaphragm. In some cases it is desirable to be able to act upon the diaphragm by using other than fluid pressure. Thus, a user may want to actuate the diaphragm independently of the presence of fluid pressure, in preparation for anticipated fluid flow. In other cases, it is desirable to maintain a diaphragm in its open position for a prescribed interval of time independently of whether fluid flow is present.

Another consideration that applies in the use of flow control devices is that the fittings used with the devices vary in tolerances. As a result, flow control valves are employed with a variety of fittings. A flow control valve that is suitable for a particular fitting may not function in the same way with a different fitting, even if the fitting is of the same general type, because of tolerance variations.

Accordingly, it is an object of the invention to enhance the control that can be achieved over fluid flow. A related object is to enhance flow control where there is a diversion of fluid flow from one direction to another.

Another object is to provide a facility for acting upon the diaphragm by using other than fluid pressure. A related object is to permit a user to actuate the diaphragm independently of the presence of fluid pressure, in preparation for anticipated fluid flow.

Still another object is to maintain a diaphragm in its open position for a prescribed interval of time independently of whether fluid flow is present.

A further object is to facilitate the use of flow control devices with fittings that vary in tolerance. A related object is to employ flow control valves with a variety of fittings. Still another related object is to permit a flow control valve that is suitable for a particular fitting to function in the same way with a different fitting, even if the fitting is of the same general type, because of tolerance variations.

A still further object is to achieve greater reliability over valve operation than is achievable by clamped diaphragms and duck-bill valves.

Yet another object is to achieve precision control at reduced cost and simplification.

An important object of the invention is to eliminate the need for needle usage at injection sites.

An additional object of the invention is to improve the performance of injection site valves.

SUMMARY OF THE INVENTION

In accomplishing the foregoing and related objects the invention provides a flow control device which includes a first channel for the flow of fluid, a branch channel connected to the first channel and angularly disposed with respect thereto to serve as a conduit for at least a portion of the flow from the first channel, a mechanism at the convergence of the branch and first channels for controlling the flow from the first channel into the branch channel, and an instrumentality for permitting the activation of the controlling mechanism by a member external to the flow control device.

In accordance with one aspect of the invention the permitting instrumentality engages the controlling mechanism is a freely floatable diaphragm bowed under pressure into the first channel. One side of the diaphragm is bowed under pressure by a prong extending in the axial direction of the first channel, and another side of the diaphragm can be bowed under pressure by the permitting instrumentality.

In accordance with another aspect of the invention the diaphragm is positioned by the prong against an annular seat and is disposable away from the annular seat by the permitting instrumentality. The seat desirably has a circumferential skirt that limits the lateral movement of the diaphragm and the permitting means is flexible.

In accordance with a further aspect of the invention the diaphragm is spaced from buttresses with respect to the diaphragm to limit the movement of the diaphragm in the axial direction of the first channel. The buttresses advantageously are equally positioned and circumferentially arranged with respect to the diaphragm.

In accordance with yet another aspect of the invention the flow control device has a channel for the flow of fluid, a branch channel angularly disposed with respect to the first channel to serve as a conduit for at least a portion of the flow from the first channel, and a freely floatable diaphragm, which is bowed under pressure into the first channel at the convergence of the branch and first channels for controlling the flow from the first channel into the branch channel.

The diaphragm is bowed under pressure by a prong extending in the axial direction of the first channel, and the diaphragm is positioned by the prong against an annular seat. The seat desirably has a circumferential skirt that limits the lateral movement of the diaphragm, which is spaced from buttresses that limit the movement of the diaphragm in the axial direction of the first channel. The buttresses advantageously are equally positioned and circumferentially arranged with respect to the diaphragm.

In accordance with a further aspect of the invention the branch channel has opposite ends, of which one end is connected to the first channel, and there is a second channel connected to the other end of the branch channel. The branch channel desirably is formed by two subordinate parallel channels.

In accordance with yet another aspect of the invention the first channel is terminated in a base and the second channel is terminated in a cap. The device is formed as a two-part member with the first part including a stem of the first channel, an outer portion of the branch channel and the cap of the second channel. The second part of the device includes a stem of the second channel, the remaining portion of the branch channel and the base of the first channel.

In a method of directionally controlling the flow of fluid by the invention, the steps include providing a first channel for the flow of fluid; providing a branch channel connected to the first channel for serving as a conduit for at least a portion of the flow in the first channel; and controlling the flow from said first channel into the branch channel by applying peripheral pressure to a diaphragm which is bowed into the first channel.

The peripheral pressure can be applied by the downward movement of a plunger against the periphery of the diaphragm. The second channel can be terminated in an injection site near the junction of the second channel with the branch channel further including the steps of self-priming the injection site by the flow of fluid from the first channel in order to clear the injection site of any prior accumulation of objectionable matter or fluid, and injecting a second fluid into the self-primed injection site.

In a method of fabricating a directional flow control device, the steps include molding a first member of the directional flow control device, including seat for a control diaphragm; molding a second member of the directional flow control device, including a support for the control diaphragm; inserting a plunger into the first member with respect to the seat of the control diaphragm; inserting the diaphragm on the seat of the first member; and joining the second member to the first member with the support for the diaphragm thereagainst.

In a method of controlling fluid flow, the steps can include introducing fluid into a first channel; diverting the fluid into a second channel; and controlling the flow of the fluid from the first channel into the second channel by applying peripheral mechanical pressure to a diaphragm which is bowed under pressure into the first channel.

A flow control device pursuant to the invention includes a first channel for the flow of fluid, a branch channel connected to the first channel to serve as a conduit for at least a portion of the flow from the first channel. A diaphragm is positioned at the convergence of the branch and first channels for controlling the flow from the first channel into the branch channel. The diaphragm is nominally positioned on a ring seat and bowed under pressure into the first channel and can be in contact with a plunger without overcoming the biasing pressure.

The first channel has a central axis and the diaphragm can be bowed under pressure by a single prong positioned along the central axis and extend into the first channel. The diaphragm can be displaced towards radially extending buttresses by the prong. The buttresses limit the extent to which pressure exerted against the diaphragm in the vicinity of the prong can force the diaphragm into the first channel.

The buttresses advantageously are equally distributed with respect to the circumference of the first channel, and the interval between the buttresses is tapered to limit the extent to which a gasseous fluid ca become entrapped between the buttresses.

In addition, radially extending buttresses can be positioned opposite the ring seat, with the diaphragm in between and extending beyond the seat. This is to limit the magnitude or diaphragm displacement.

The buttresses can be positioned in a closed end of the first channel, extending radially from the central axis of the first channel, while being circumferentially disposed with respect to the first channel. The buttresses can be equal distributed with respect to the circumference of the first channel, with the interval between the buttresses forming the closed end and being tapered to limit the extent to which a gaseous fluid can become entrapped between the buttresses.

The second channel can be terminated in a cap which has a central surface communicating with the second channel, and a branch channel can have a flow surface that is aligned with the central surface of the cap to provide for the purging of the second channel by flow into the first channel through the branch channel and across the central surface of the cap.

In a method of directionally controlling the flow of fluid, the steps include providing a first channel for the flow of fluid; providing a branch channel, connected to the first channel, for serving as a conduit for at least a portion of the flow in the first channel; and controlling the flow from the first channel into the branch channel by a diaphragm which is restricted from being sucked into the branch channel. The second channel can be terminated in an injection site near the junction of the second channel with the branch channel to permit the self-priming of the injection site by the tangential flow of fluid from the first channel across the injection site in order to clear the injection site of any prior accumulation of objectionable matter or fluid.

A flow control device of the invention can include a first channel for the control of fluid; a ring seat within the first channel; a plunger within the first channel; a control diaphragm in tangential contact with the ring seat and the plunger; with the ring seat sloping away from the control diaphragm on both sides of the tangential contact. Radially extending buttresses can be positioned opposite the ring seat, with the diaphragm between the buttresses and the ring seat. The radially extending buttresses can be circumferentially disposed about the first channel, and extend o both sides of the tangential contact of the diaphragm with the ring seat.

In a method of controlling fluid flow, the steps include introducing fluid into a first channel; diverting the fluid into a branch channel to create a stream of flow that makes tangential contact with an injection site internal surface that is in alignment with a passageway surface of the branch channel. This is to purge the injection site from unwanted substances. In a further method of controlling fluid flow in accordance with the invention, fluid is introduced into a first channel; diverted into a second channel; and the flow of fluid from the first channel into the second channel is externally controlled by acting against a diaphragm which is bowed under pressure into the first channel.

DESCRIPTION OF THE DRAWINGS

FIG. 1A is a cross-sectional view of a directional flow-control valve and coupling device in accordance with the invention;

FIG. 1C is a perspective view of the flow control device of FIGS. 1A and 1B in use in accordance with the invention;

FIG. 3B is a cross-sectional view of the directional flow control and coupling device of FIG. 3A employing the plunger of FIG. 2B, taken along the lines 3B—3B; and FIG. 3C is a cross-sectional view of the directional flow control and coupling device of FIG. 3A employing the plunger of FIG. 2C, taken along the lines 3B—3B.

Figure 1B:
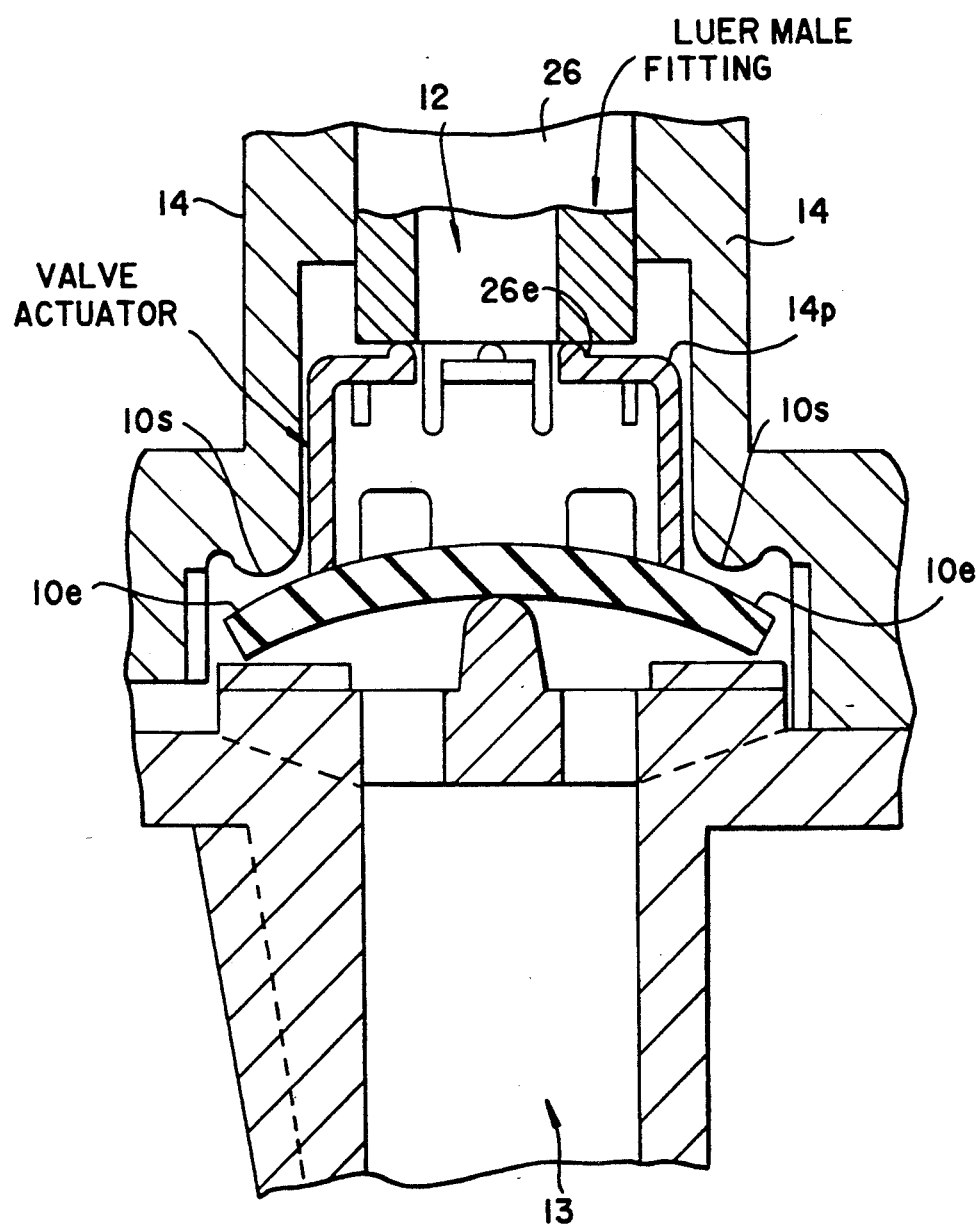
FIG. 1B is an enlarged fragment of FIG. 1A illustrating the action of an internal plunger against the diaphragm of the device in FIG. 1A.

DETAILED DESCRIPTION (a) First Embodiment of the Invention

With reference to the drawings, a coupling device 10 in accordance with the invention is shown in FIG. 1A. The device 10 is formed by a base 10b and a cap 10c. The cap 10c contains respective apertures 11a and 12a for a first flow channel 11 and a branch flow channel 12. The aperture 12a can serve as an injection site for the branch channel 12.

The cap 10c also includes a mount or housing 14 that contains a plunger 14p and receives a flow input fitting (not shown in FIG. 1A), such as a tubing or a Luer fitting. Flow from the respective channels 11 and 12 is selectively combined in an output channel 13 in accordance with the operation of a control diaphragm 10d. The diaphragm 10d seals the channel 11 when there is upward flow in the channel 13. This kind of diaphragm operation is commonly provided by a check valve but in FIGS. 1A and 1B is provided by the multifunctional coupling structure 10. In the channel 12, when the plunger 14p is moved downwardly, or there is downward flow in the channel 12 through the housing 14, the diaphragm 10e is unseated. In either case, the diaphragm 10e is moved away from its seat 10s in the cap 10c as pictured in FIG. 1B, which illustrates the role of the plunger 14p in opening the diaphragm 10e. Conversely, when plunger 14p moves to its upward, withdrawn position, the diaphragm 10e is reseated. Alternatively when downward flow is terminated, the diaphragm 10e is reseated.

In order to properly seat the diaphragm 10d when there is no downward flow, the base member 10g includes prebiasing prongs 10p on a platform 10f of the base 10b. "Prebiasing" means that there is a small force, i.e., bias, exerted against the diaphragm 10d by the prongs 10p when the diaphragm is in its equilibrium position.

The channel 12 can be an injection site for the introduction of a substance to be mixed with fluid flowing in the channel 13. In addition to having the diaphragm 10e opened by flow, the invention provides the internal plunger 14p which can be actuated externally of the device 10, for example by a Lauer fitting 16 as shown in FIG. 1C. The end 16e of the Lauer fitting engages the end of the plunger 14p, and pushes it downwardly to open the diaphragm independently of whether there is downward fluid flow.

The combination injection site and the check valve in FIGS. 1A through 1C achieves a number of advantages. The close proximity of the site and valve prevents any retrograde flow and improves purging. This is important in the case of drugs that require minimum diluent, or that must be administered quickly to a patient. In the case of viscous and highly dense drugs that flow from intravenous tubing, a considerable amount of time and fluid are required in order to purge the drug out of tubing. It is important to minimize any stagnant area where drugs or air can collect. This avoids air entrapment.

(b) Second embodiment of the Invention

Figure 2A:
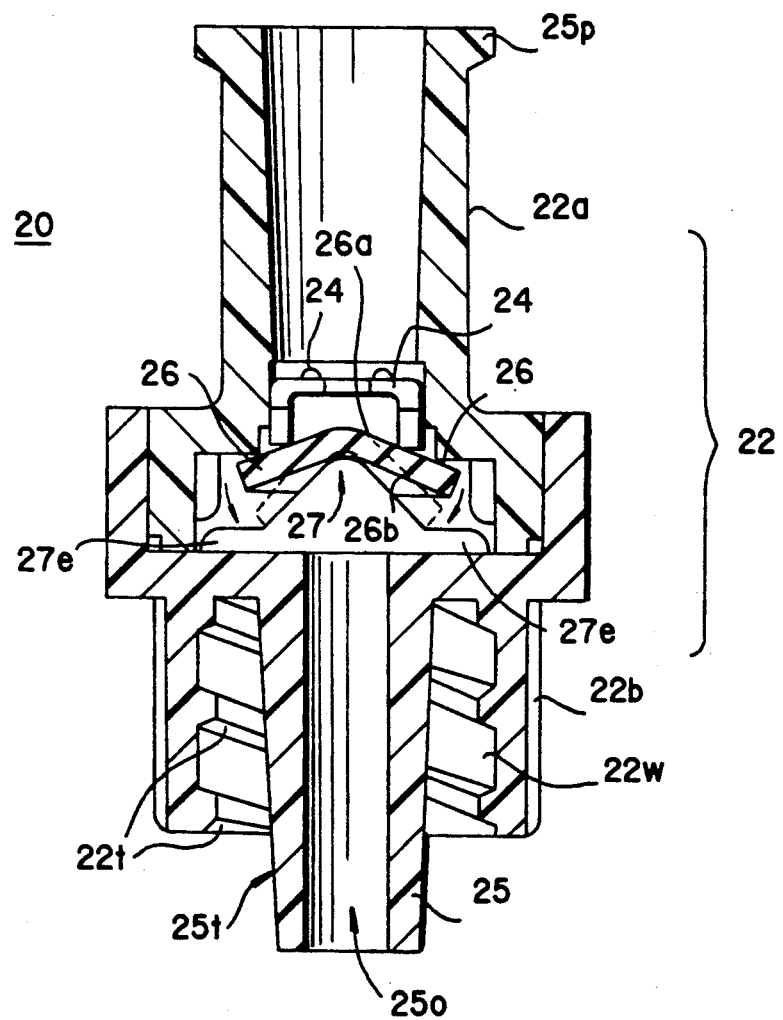
FIG. 2A is a cross-sectional view of an alternative coupling device in accordance with the invention.

An alternative flow control device 20 in accordance with the invention is shown in FIG. 2A. In the device 20, there is a housing 22 with two parts 22a and 22b. The part 22a includes a plunger 24 and a flexible disc 26. The plunger 24 serves to permit opening of the disc 26 externally of the device 20, by, for example a Luer fitting of the kind used in FIG. 1C. Generally, the device 20, like the device 10 of FIG. 1A, can be used for continuous intravenous fluid administration to a patient.

Figure 3A:
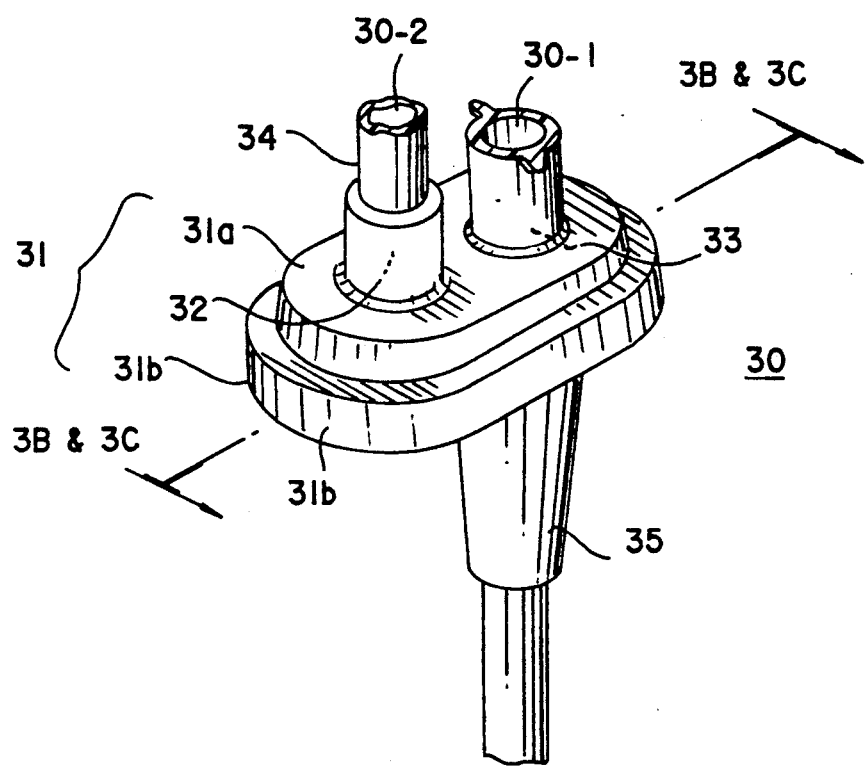
FIG. 3A is a perspective view of a modified flow control device of FIG. 1B in use in accordance with the invention.

When therapy of a patient requires supplemental intravenous medication, or other intermittent fluid administration, the device of FIG. 2A is modified by including a branch, similar to that of FIG. 1A or 3A, so that a syringe or other injection apparatus can be used to insert medication into the intravenous fluid. This is accomplished by inserting an injector into a branch channel. Since an intravenous solution may be administered for lengthy periods, any closure used in the branch channel desirably should withstand numerous injections, even under high pressure.

The housing 22 accommodates both the flexible plunger 24 and the valve diaphragm 26. The flexible plunger 24 within the housing 22a is shown in detail in FIG. 2B. The plunger 24 includes a top 24t, a cylindrical retainer 24r, an intermediate ledge 24d and a tabbed inlet 24c. The tabs of the inlet 24c are specially designed to receive the end 26e of the Luer fitting 26 shown in FIG. 1B. The use of a flexible coupling is important to assure that the Luer filling will seal the inlet t the injection site and simultaneously act upon the plunger. In the absence of a flexible plunger, because of tolerance variations, some Luer tapes will seal the inlet without making contact with the plunger. Because of the flexible tabs, the Luer filling is devised of making the necessary seal with the inlet and simultaneously open the associated diaphragm. Thus, for some cases of a rigid plunger, the diaphragm could be forced completely against the diaphragm without making the necessary seal. In other cases the seal could be made before the desired contact with the plunger.

Illustrative details of a Luer coupling are shown with respect to the body portion 22b of the device in FIG. 2A. The body portion 22b has an inner wall 22w provided with threads 22t for attachment to a suitable flow structure. The central tubular portion 25 has an inner outlet opening 25o and an outer Luer taper 25t.

The coupling of a Luer taper to a valve inlet is illustrated with respect to the body portion 22a of FIG. 2A. The outer end of the body portion 22a has projections 25p which are engaged by the treads 22t of the wall 22w of the body portion 22b. It is apparent that when a Luer fitting, with for example, the Luer taper 25t is threaded on the body portion 22a, the tip of the fitting engages the inlet 25c of the plunger 25. Simultaneously, the taper 25t of the Luer extension 25 engages the inner walls of the channel extending within the body portion 22a. Because of tolerance variations, the taper may engage the inner walls before there is contact with the plunger, or may engage the plunger insufficiently to open the diaphragm 26. In order to remedy this possibility the invention provides for flexibility in the plunger 24. This flexibility is achieved by the use of flexible tabs in the plunger so that the initial pressure exerted by the Luer tip provides initial depression of the tabs and assures sufficient downward movement of the plunger against the diaphragm.

Structurally the disc 26 has opposed surfaces 26a and 26b. A prong 27 with lateral extensions or buttresses 27e is affixed to the lower body element 22b. The purpose of the buttresses 27e is to assure that when the disc 26 is open, there will be an adequate passage for liquid flow about the peripheral edge of the disc 26.

The component elements of the device 20 are joined, for example, by ultrasonic welding. Upon assembly the upper tip of the prong 27 applies pressure to the diaphragm or disc 26, which tends to be held in position against the plunger 24. Preferably the pressure by the prong 27, coupled with the action of the plunger 24, tends to restrain the disc from side-to-side movement.

Figure 2B:
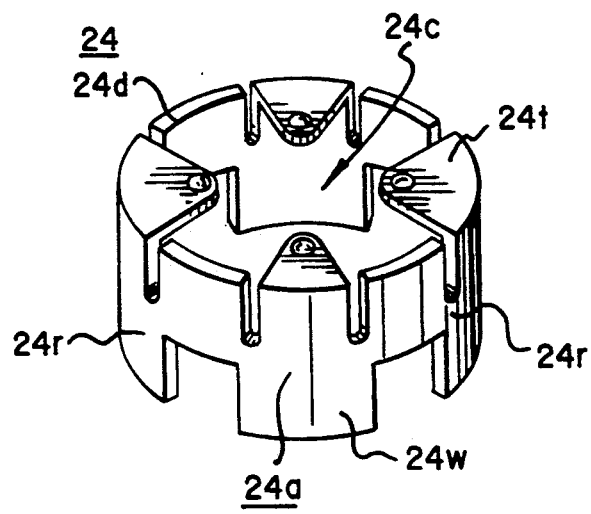
FIG. 2B is a perspective view of a plunger for the valve of FIG. 2A.

With respect to the plunger 24 as shown in FIG. 2B, the body portion 24a includes a skirt or side wall 24w that is apertured at its base and extends circumferentially with downwardly turned tabs at its top. The plunger 24 is approximately cylindrically-shaped with a grooved bottom that engages the diaphragm. The top of the housing 22a, together with the end of the plunger 24 in the ledge 22d, hold the disc 26 in position against the prong 27.

Figure 2C:
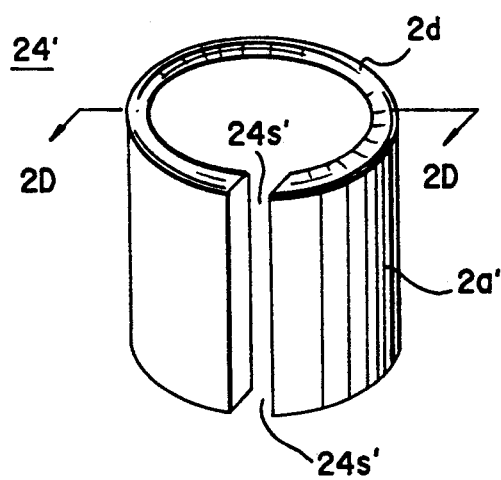
FIG. 2C is a perspective view of an alternative plunger for the valve of FIG. 2A.
Figure 2D:
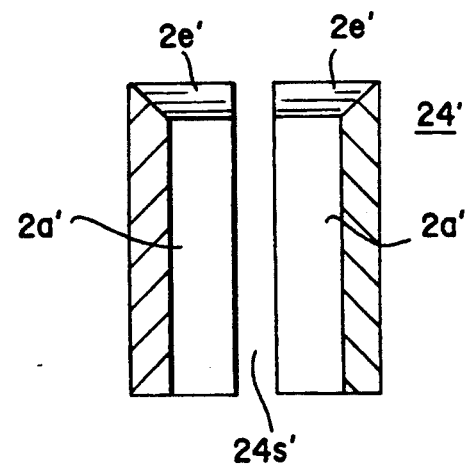
FIG. 2D is a sectional view of the plunger of FIG. 2C taken along the lines of 2D—2D.

An alternative plunger 24, is shown in FIG. 2C. The body portion 24a' omits the skirt or side wall 24w of FIG. 2B. The plunger 24, is approximately cylindrically-shaped with a longitudinal split 24s' which provides flexibility when the plunger 24' is engaged by a luer fitting. In order to allow for tolerance variations in the valve housing with respect to the luer fitting, the upper edge 24e' of the plunger 24' is beveled as indicated in FIG. 2D. Consequently, when the luer fitting engages the plunger 24', any variation in tolerances is accommodated by a expansion or widening of the split 24s'. Thereafter, when the valve is to be opened, the luer fitting is threaded against its receptacle housing causing pressure to be transmitted through the plunger 24' to the diaphragm below which is contacted by the lower edge 24e $\propto$ of the plunger 24'. When the plunger 24' is used in the valve of FIG. 2A, the top of the housing 22a, together with the end of the plunger 24', hold the disc 26 in position against the prong 27.

Alternatively, the body portion 22a may be provided with a structure of the type shown and described in U.S. Pat. No. 4,415,003.

(c) Third Embodiment of the Invention

In order to simplify directional flow control, the invention also provides the two-part devices 30 and 30' shown in FIGS. 3A, 3B and 3C, with a first flow channel 30-1 and a second flow channel 30-2.

The device 30 includes a first part 31a joined to a second part 31b by ultrasonic welding. Within the device 30 are a flow control diaphragm 32 and an injection site diaphragm 33.

The diaphragm 32 is housed on one side by an inlet sleeve 34 of the part 31a that surrounds supporting structure in the part 31b. A horizontal passageway within the housing 31 extends from the inlet sleeve 34 to an outlet sleeve 35. Fluid flows vertically downward in the sleeve 34, around the diaphragm 32 into the horizontal passageway of an extension 36, then downwardly through the outlet sleeve 35. As a result, tubing attached to the inlet sleeve 34 of the housing, and to the outlet sleeve 35 of the housing are approximately parallel to one another.

Since the tubing generally hangs vertically, the injection site diaphragm 33 generally is positioned near the top of the housing 31 where it is easily accessible to medical personnel. As an intravenous solution leaves the valve within the housing 31, it makes an approximately right-angle turn and moves directly across the bottom of the injection site diaphragm 33. The fluid flow forces substantially all air below the site 33 into the outlet sleeve 35. The injection site is thus self-priming. In a number of prior art injection sites, particularly those with sleeve stoppers, cavities located at the centers of the stoppers prevented self-priming. With a sleeve stopper, even a liquid stream directed across the bottom of the stopper cannot expel air located within a cavity. Air has to be removed in such a case by inverting the injection site, while manually tapping the housing.

A cross-sectional view of one embodiment of the device 30 is shown in FIG. 3B. The injection site, which is like those of FIGS. 1B and 2B, promotes sterility by providing ease of accessibility. Prior art injection sites with stoppers recessed below the tops of injection sites allow antimicrobial agents to accumulate in puddles on the tops of stoppers. Particulate matter may also collect on recessed stoppers and be transmitted from the injection site to intravenous solution when the stopper is pierced by a needle. A raised site, with an associated Leur closure (of the kind shown in FIGS. 1A, 1C, 2A and 3A), guards against the presence of microbial agents.

In addition, as shown in FIG. 3B, the injection site provides a preferred target for injection. The housing 31a with the injection site is molded as one unit and forms a suitable closure for the site. In addition, the unitary housing 31a extends to a Leur sleeve 33s, as well as to the inlet sleeve 34. The Housing 31a also forms a cover 37 for the passageway 36 that extends from the diaphragm 32 to the vicinity of the base of the site 33.

To complete the structure 30, a unitary housing 31b is ultrasonically welded to the upper housing 31a. The ultrasonic welds are at the base of a trough which extends completely around the upper portion of the housing 31b. Because the device 30 is formed by the two-part housing 31, assembly of the device is relatively simple as compared with the complexity of assembly required for the prior art. The assembly is readily accomplished by inserting the plunger 14p and the diaphragm 33 into the cap of the member 31a, and simultaneously inserting the diaphragm 32 against a ring seat of the sleeve 34. The second member 31b is then seated against the member 31a and the ultrasonic welding accomplished. By contrast with prior art directional flow control valves, the diaphragm 32 is freely floatable and is not pinned to one side of the valve structure. The free floatability of the diaphragm 32 assures positive seating of the diaphragm, which is under a perscribed amount of bias, i.e., equilibrium pressure provided by the central pin 32p in the base of the member 31b. In addition, the base includes butresses or ledges 34b which limit the extent to which the diaphragm is opened by pressure in the inlet sleeve 34. Once the diaphragm 32 is opened, the inlet flow is guided by the dual passageway 36-1 and 36-2 to the base of the site 33 at the end of the outlet sleeve 35.

A cross-sectional view of FIG. 3B taken along the lines A—A shows the dual channel passageway between the diaphragm and the site 33, along with the buttresses 34b.

In a further embodiment of the flow control device of FIG. 3A, as shown in FIG. 3C, the plunger 14p of FIG. 3B has been replaced by an alternative plunger 14p, corresponding to the plunger of FIGS. 2C and 2D.

Other aspects of the invention will be apparent to those of ordinary skills in the art.

What is claimed is:

1. The method of controlling fluid flow in a device which includes the steps of:
   (1) introducing fluid into an input channel;
   (2) diverting said fluid into an output channel; and
   (3) controlling the flow of said fluid from said input channel into said output channel by applying peripheral mechanical pressure to a diaphragm which is bowed under pressure into said input channel, wherein said peripheral pressure is applied by further engaging an internal member in contact with said diaphragm by an external member after absorbing the initial engagement to compensate for tolerance variations between.

2. The method of claim 1 for controlling the flow of fluid which comprises the steps of
   (a) providing an input channel for the flow of fluid;
   (b) providing a branch channel connected to said input channel for serving as a conduit for at least a portion of the flow in said input channel; and
   (c) controlling the flow from said input channel into said branch channel by applying peripheral pressure to a diaphragm which is bowed into said input channel by simultaneously engaging said diaphragm by a split cylinder internal member and widening the split of said cylinder.

3. The method of claim 2 wherein said branch channel includes a plunger engaging a further diaphragm and peripheral pressure is applied by the downward movement of said plunger against the periphery of said further diaphragm.

4. The method of claim 2 wherein said branch channel is terminated in an injection site near the junction of said input channel with said branch channel further including the steps of self-priming said injection site by the flow of fluid from said input channel in order to clear said injection site of any prior accumulation of objectionable matter or fluid, and injecting a second fluid into the self-primed injection site.

5. The method of directionally controlling the flow of fluid in accordance with claim 10 which comprises
   controlling the flow from said input channel into said branch channel by a diaphragm and restricting said diaphragm from being sucked into said branch channel.

6. The method of claim 5 wherein said branch channel is terminated in an injection site further including the steps of self-priming said injection site by the tangential flow of fluid from said input channel across said injection site in order to clear said injection site of any prior accumulation of objectionable matter or fluid, and injecting a second fluid into the self-primed injection site.

7. The method of controlling fluid flow in accordance with claim 4 which comprises the steps of:
   (1) introducing fluid into an input channel;
   (2) diverting said fluid into a branch channel to create a stream of flow that makes tangential contact with an injection site internal surface that is in alignment with a passageway surface of said branch channel in order to purge the injection site from unwanted substances.

8. The method of directional flow control which comprises the steps of:
   (a) directing flow into a first housing, including a seat for a fluid pressure control diaphragm and a separate seat for an injection control diaphragm, with the diaphragms on the seats of said first housing;
   (b) directing said flow into a second housing, including supports for the control diaphragms, with said second housing joined to said first housing with said supports for said diaphragms thereagainst; and
   (c) flexing a plunger inserted into said first member with respect to said injection control diaphragm.

9. The method of controlling fluid flow in a device with input and output channels, which comprises the steps of:
   providing an internal member for the control of flow between said input and output channels; and
   activating the control over flow by a member external to said device after using said internal member to compensate for tolerance variations in the external member.

10. The method of claim 9 wherein said internal member engages a diaphragm between said input and output channels and the step of compensating for tolerance variations comprises expanding said internal member.

11. The method of claim 10 wherein said external member is a Luer fitting and the step of compensating for tolerance variations comprises flexing said plunger by said Luer fitting.

12. The method of claim 9 wherein said device includes a plunger in engagement with a diaphragm of said controlling means and the step of compensating for tolerance variations comprises flexing said plunger.

13. The method of claim 12 wherein said plunger includes a body with a split therein and the step of flexing said plunger comprises expanding said split.

14. The method of claim 13 wherein the split of said plunger extends longitudinally and said step of flexing said plunger comprises expanding said longitudinal split in said body.

15. The method of claim 12 wherein said plunger includes a beveled surface and the step of flexing said plunger includes the step of engaging said beveled surface by said external member.

16. The method of claim 12 wherein the step of compensating for tolerance variations includes simultaneously sealing the input channel.

17. The method of claim 9 further including an injection site between said input and output channels, further including the step of clearing said injection site of any prior accumulation of objectionable matter by tangential fluid flow at said injection site.

18. The method of claim 17 wherein a branch channel is included between said input and output channels and said input channel contains a diaphragm under pressure with a central surface communicating with said branch, further including the step of purging said output channel by flow into said first channel through said branch channel and across said central surface.

19. The method of claim 9 wherein the step of compensating for tolerance variations comprises absorbing the initial engagement of said external member before activating said control.

* * * * *